US00PP15482P2

(12) United States Plant Patent
Olesen et al.

(10) Patent No.: US PP15,482 P2
(45) Date of Patent: Jan. 18, 2005

(54) CLIMBING ROSE PLANT NAMED 'POULYC007'

(50) Latin Name: *Rosa hybrida*
Varietal Denomination: POULyc007

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/719,707

(22) Filed: Nov. 21, 2003

(51) Int. Cl.[7] ..... A01H 5/00
(52) U.S. Cl. ..... Plt./114
(58) Field of Search ..... Plt./114, 109

*Primary Examiner*—Anne Marie Grunberg
*Assistant Examiner*—June Hwu

(57) ABSTRACT

A new climbing garden rose plant which has abundant, pink flowers and attractive foliage. This new and distinct variety has shown to be uniform and stable in the resulting generations from asexual propagation.

2 Drawing Sheets

Botanical classification: *Rosa hybrida.*
Variety denomination: 'POULyc007'.

SUMMARY OF THE INVENTION

The present invention constitutes a new and distinct variety of garden rose plant which originated from a controlled crossing between a female parent 'POULsint', an unpatented variety, and the male parent, an unnamed plant. The two parents were crossed during the summer of 1994, and the resulting seeds were planted in a controlled environment in Fredensborg, Denmark. The new variety is named 'POULyc007'.

The new variety may be distinguished from its seed parent, 'POULsint', by the following combination of characteristics:

1. The female parent has a flower diameter when open of less than 5 cm. 'POULcy007' has flowers which are 75 mm in diameter when open.
2. While the seed parent has a narrow and bushy growth habit, 'POULcy007' has a climbing habit.

The new variety may be distinguished from its pollen or male parent, an unnamed plant, by the following combination of characteristics:

1. The male parent has a flower petal color, on open flowers, upper surface of White Group 155D. 'POULyc007' has a flower petal color on open flowers, upper surface of Red Group 55C.
2. General tonality of the pollen parent is opening are White Group 155B, while 'POULyc007' has a general tonality of Red Group 55D.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;
3. Disease resistance.
4. Improved flowering habit. Since the variety is less apically dominant, flowers are produced evenly from the lower branches to the top.

This combination of qualities is not present in previously available commercial cultivars of this type, known to the inventor, and distinguish 'POULyc007' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULyc007' was selected in the spring 1995 by the inventors as a single plant from the progeny of the aforementioned hybridization.

Asexual reproduction of 'POULyc007' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULyc007' are true to type and are transmitted from one generation to the next.

BRIEF DESCRIPTION OF THE DRAWING

The accompanying colored illustration shows as true as is reasonably possible to obtain in color photographs of this type, the typical characteristics of the buds, flowers, leaves, and stems, of 'POULyc007'. Specifically illustrated in SHEET 1 are:

FIG. 1.1; Open flower, stem showing branching, open flower, the attachment of buds, and peduncles;

FIG. 1.2; Flower petals, detached;

FIG. 1.3; Sepals, receptacle, and pedicel;

And specifically illustrated in SHEET 2 are:

FIG. 2.1; Flower buds closed, flower bud as sepals unfold and partially open flower.

FIG. 2.2; Juvenile Flower buds and growth showing anthocyanin.

FIG. 2.3; Juvenile leaves with anthocyanin;

FIG. 2.4; Mature leaves;

FIG. 2.5; Bare stems with thorns.

DETAILED DESCRIPTION OF THE VARIETY

The following is a description of 'POULyc007', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULover', a rose variety from the same inventors described and illustrated in U.S. Plant patent application Ser. No. 10/341,890 and dated Jan. 13 , 2003, are compared to 'POULyc007' in Chart 1.

CHART 1

| | 'POULyc007' | 'POULover' |
|---|---|---|
| Bud color as sepals unfold | Petals are Red Group 46C with intonations of Red Group 46C; at ¼ opening, petals are Red Group 48A. | Petals are Red Group 55C; at ¼ opening, petals are Red Group 55C. |
| Receptacle Color | Yellow-Green Group 144B. | Yellow-Green Group 144A. |
| Outermost Petals upon opening, outer side | Red Group 52B. | Red-Purple Group 65A at petal margins. Red-Purple 65D at mid petal. |

Parents:

*Seed parent.*—POULsint.

*Pollen parent.*—Unnamed Plant.

FLOWER AND FLOWER BUD

Blooming habit: Continuous.

Flower bud:

*Size.*—Upon opening, 22 mm in length from base of receptacle to end of bud. Average diameter is 13 mm.

*Bud form.*—Broad based.

*Bud color.*—As sepals unfold, petals are Red Group 46C with intonations of Red Group 46A. Red Group 48A at ¼ opening. Sepals: Shape: Subulate with outward extending foliaceous appendages. Upper Surface: Color: Yellow-Green Group 145B. Observations: Surfaces of sepals moderately pubescent. Stipitate glands are very abundant in quantity and characterized by a distinctive spicy fragrance. Lower Surface: Color: Yellow-Green Group 144A. Anthocyanin: Very strong, Greyed-Purple Group 187A. Margin: Margins have strong foliaceous appendages on three of the five sepals. Size: 22 mm long by 8 mm wide.

*Receptacle.*—Surface Texture: Smooth and glabrous. Shape: Urn-shaped. Size: 7 mm (h)×7 mm (w). Color: Yellow-Green Group 144B. Anthocyanin: Greyed-Red Group 181A.

*Peduncle.*—Surface: Many stipitate glands, characterized by a distinct spicy fragrance observed. Length: 30 to 35 mm average length. Diameter: 2.5 mm average. Color: Greyed-Red Group 183A and Yellow-Green Group 144B. Strength: Strong.

*Borne.*—Multiples of 9 buds per flowering stem.

Flower bloom:

*Fragrance.*—Moderate rose.

*Duration.*—The blooms have a duration on the plant of approximately 10 to 14 days. After flowers have fully matured, petals drop cleanly away from the receptacle.

*Size.*—Average flower diameter is 75 mm when open.

*Form.*—Rosette with overlapping petals.

*Shape of flower when viewed from the side.*—Upon opening, upper part: Flat. Upon opening, lower part: Flattened convex. Open flower, upper part: Convex. Open flower, lower part: Concave.

Petalage: Very double. Average range: 50–55 petals under normal conditions with 10 petaloids.

Color: Upon opening, petals:

*Outermost petals.*—Outer side: Red Group 52B with vertical intonations of Red Group 46A. Inner Side: Red Group 52C.

*Innermost petals.*—Outer side: Red Group 52B. Inner Side: Red Group 52C.

Upon opening, basal petal spots:

*Outermost petals.*—Outer side: Yellow Group 1C to 1B. Inner side: Yellow Group 1C to 1B.

*Innermost petals.*—Outer side: Yellow Group 1C to 1B. Inner Side: Yellow Group 1C to 1B.

After opening, petals:

*Outermost petals.*—Outer side: Red Group 55C. Inner Side: Red Group 56A.

*Innermost petals.*—Outer side: Red Group 55C. Inner Side: Red Group 56A.

After opening, basal petal spots:

*Outermost petals.*—Outer side: Yellow Group 1C to 1B. Inner side: Yellow Group 1C to 1B.

*Innermost petals.*—Outer side: Yellow Group 1C to 1B. Inner Side: Yellow Group 1C to 1B.

General tonality: On open flower Red Group 55D. No change in the general tonality at the end of the $10^{th}$ day. Afterwards, general tonality is Red Group 55D.

Petals:

*Petal reflex.*—Petals reflex somewhat strongly.

*Margin.*—Entire with medium undulations of margin.

*Shape.*—Apex: Round. Base: Acute.

*Size.*—37 mm (l)×35 mm (w).

*Texture.*—Smooth.

*Thickness.*—Average.

*Arrangement.*—Not Formal.

Petaloids:

*Quantity.*—10–15.

*Size.*—33 mm (l)×25 mm (w).

*Color.*—Upper Surface: Red Group 56A. Lower surface: Red Group 55C.

Reproductive organs:

*Pistils.*—Length: 9 mm long. Quantity: 64 (actual count).

*Pollen.*—None observed.

*Anthers.*—Size: 2 mm long. Color: Yellow-Orange Group 17A. Quantity: 56 (actual count).

*Filaments.*—Color: Yellow Group 6A. Length: 3 mm.

*Stigmas.*—Superior in relation to the height of the anthers. Color: Yellow-Green Group 154D.

*Styles.*—Color: Yellow-Green Group 154D. Other intonations: None.

*Hips.*—None Observed in the field nursery in Jackson County Oreg.

PLANT

Plant growth: Vigorous. Very, very tall climbing habit of 200–300 cm in height. Weak apical dominance allows flowers to develop evenly from lower branches to the top.

Stems:

*Color.*—Juvenile Stem: Yellow-Green Group 144B with intonations of Greyed-Purple 185A. Mature Stem: Yellow-Green Group 144B.

*Thorns.*—Incidence: 12 thorns per 10 cm of stem. Size: Average length: 5 mm. Mature Thorn Color: Greyed-Yellow Group 160A. Juvenile Thorn Color: Greyed Red Group 179B with Greyed Yellow Group 160A. Shape: Deeply concave.

*Surface texture.*—Young wood: Smooth. Older wood: Smooth.

Plant foliage: Normal number of leaflets in middle of the stem: 7.

*Compound leaf size.*—38 mm (l)×30 mm (w).

*Color.*—Mature Foliage: Upper Leaf Surface: Yellow-Green Group 147A. Lower Leaf Surface: Yellow-Green Group 147C. Juvenile foliage: Upper Leaf Surface: Yellow-Green Group 146B to 146C. Lower Leaf Surface: Yellow-Green Group 146C. Anthocyanin: Juvenile foliage exhibits anthocyanic intonations of Greyed-Orange Group 173A.

Plant leaves and leaflets:

*Stipules.*—Size: 26 mm. Color: Yellow-Green Group 144A. Margins: Serrate. Stipitate Glands: Medium. Shape: Linear with outward extending apecies.

*Petiole.*—Length: 35 mm. Diameter: 2 mm. Color: Yellow-Green Group 144B. Anthocyanin: None Observed. Underneath: Thorns and stipitate glands observed.

*Rachis.*—Length: 35 mm. Color: Yellow-Green Group 144B. Anthocyanin: None Observed.

*Leaflet.*—Size: Terminal leaflets are typically 50 mm (l)×35 mm (w). Edge: Serrated. Shape: Generally ovate to round. Apex: Cuspidate. Base: Round. Texture: Smooth. Arrangement: Odd pinnate. Venation: Reticulate. Glossiness: Glossy.

Disease resistance: Above average resistance to mildew, rust, black spot, and Botrytis under normal growing conditions in Jackson County, Oreg.

Cold hardiness: The variety 'POULyc007' has been found to be cold tolerant to USDA Cold Hardiness Zone 6.

It is claimed:

1. A new and distinct variety of rose plant of the climbing rose class, substantially as herein illustrated and described as a distinct and novel rose variety due to its abundant light pink flowers, disease resistance, and extended period of bloom.

* * * * *

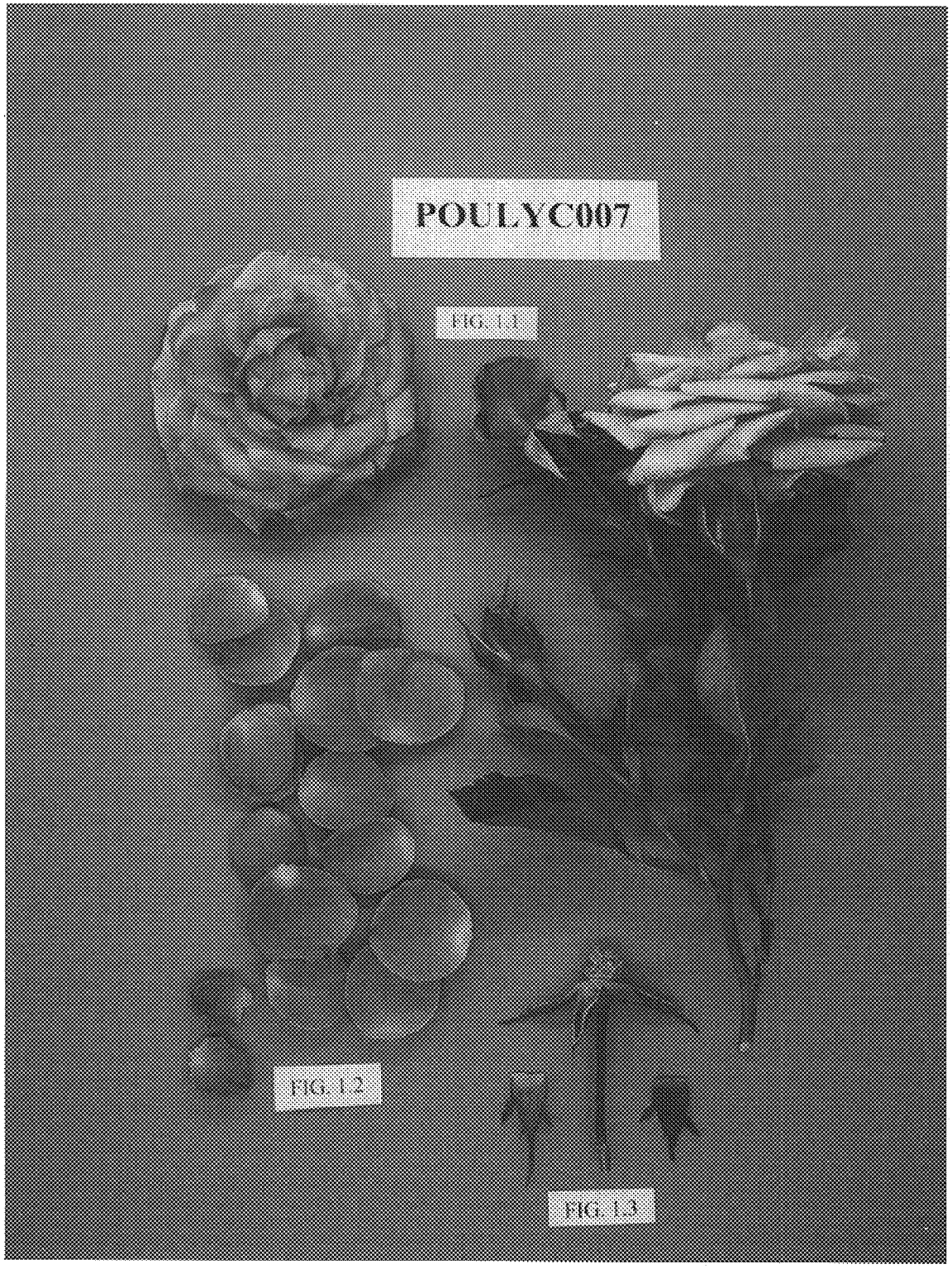
POULYC007
FIG. 1.1
FIG. 1.2
FIG. 1.3

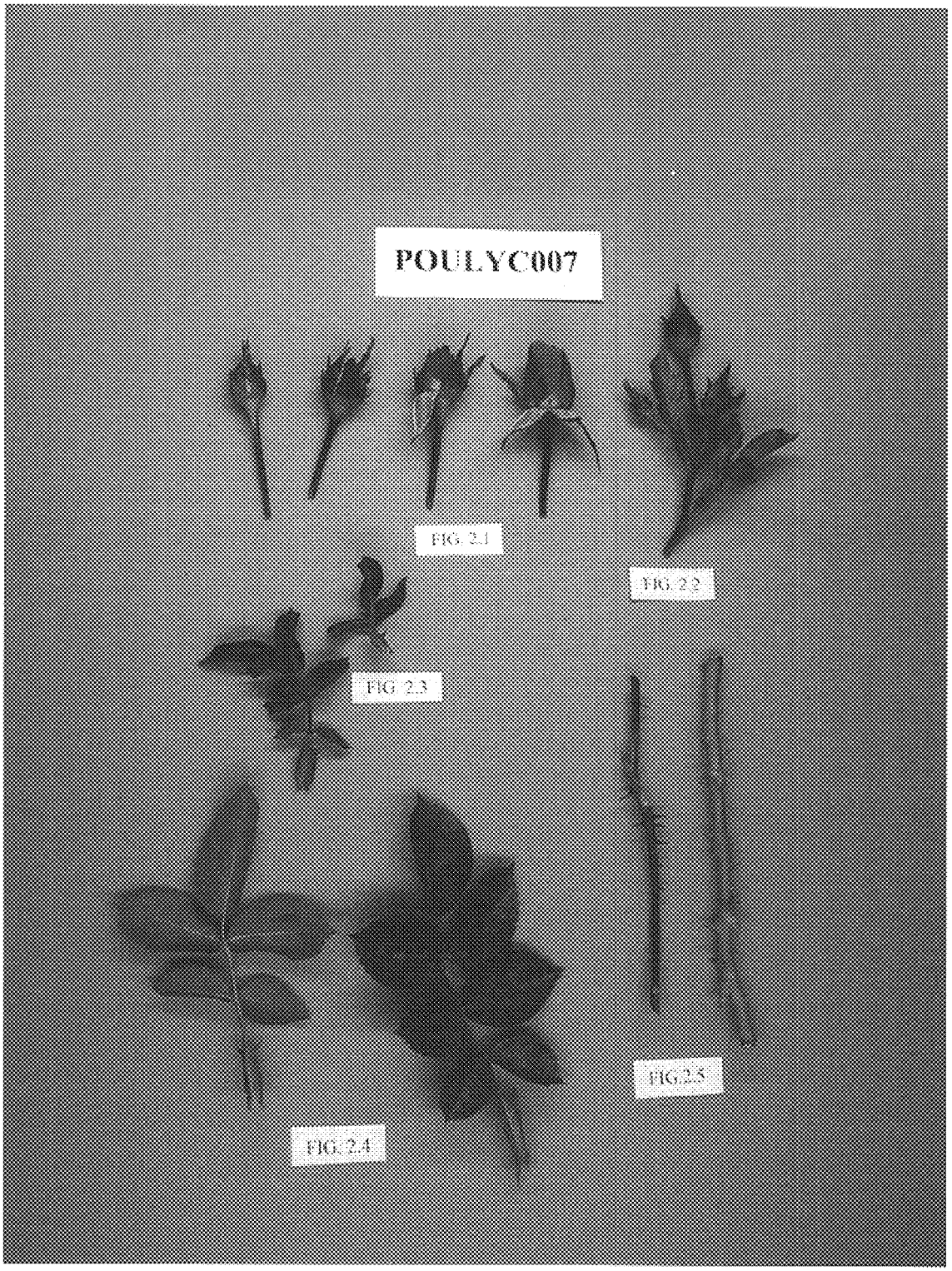
POULYC007
FIG. 2.1
FIG. 2.2
FIG. 2.3
FIG. 2.4
FIG. 2.5